(12) United States Patent
Nimgaard et al.

(10) Patent No.: US 8,603,071 B2
(45) Date of Patent: Dec. 10, 2013

(54) LOCKING DEVICE FOR SHEATH OR CATHETER

(75) Inventors: Lars S. Nimgaard, Koege (DK); Bent Ohlenschlaeger, Lille Skensved (DK); Erik E. Rasmussen, Slagelse (DK)

(73) Assignee: Cook Medical Technologies LLC, Bloomington, IN (US)

( * ) Notice: Subject to any disclaimer, the term of this patent is extended or adjusted under 35 U.S.C. 154(b) by 645 days.

(21) Appl. No.: 12/082,534

(22) Filed: Apr. 11, 2008

(65) Prior Publication Data

US 2008/0255542 A1 Oct. 16, 2008

Related U.S. Application Data

(60) Provisional application No. 60/922,789, filed on Apr. 11, 2007.

(51) Int. Cl.
*A61M 25/16* (2006.01)

(52) U.S. Cl.
USPC .......................................................... 604/535

(58) Field of Classification Search
USPC ............ 604/263, 523–533, 535, 264, 165.01, 604/164.1
See application file for complete search history.

(56) References Cited

U.S. PATENT DOCUMENTS

| 5,064,414 | A | 11/1991 | Revane |
| 6,641,564 | B1 * | 11/2003 | Kraus ........................ 604/164.1 |
| 7,300,454 | B2 * | 11/2007 | Park et al. ..................... 623/1.11 |
| 2002/0147429 | A1 * | 10/2002 | Cowan et al. ................. 604/187 |
| 2007/0123971 | A1 | 5/2007 | Kennedy, II |
| 2009/0198192 | A1 * | 8/2009 | Uematsu et al. .............. 604/187 |

FOREIGN PATENT DOCUMENTS

| WO | WO2004/021930 | 3/2004 |
| WO | WO2006/007389 | 1/2006 |
| WO | WO2007/004076 | 1/2007 |
| WO | WO2007/005799 | 1/2007 |
| WO | WO2007/058816 | 5/2007 |
| WO | WO2007/127351 | 11/2007 |

OTHER PUBLICATIONS

International Search Report, PCT/US2008/004733, Nov. 10, 2008, Wm. Cook Europe ApS.
Written Opinion, PCT/US2008/004733, Nov. 10, 2008, Wm. Cook Europe ApS.
Int'l Prelim Report on Patentability, PCT/US084733, Jul. 29, 2009, Wm. Cook Europe ApS.

* cited by examiner

*Primary Examiner* — Kevin C Sirmons
*Assistant Examiner* — Imani Hayman
(74) *Attorney, Agent, or Firm* — Richard J. Godlewski

(57) ABSTRACT

There is disclosed a locking unit (100) for locking a pusher (128) to a sheath assembly (164). The locking unit (100) includes a longitudinal locking portion (102) and a radial locking portion (104). The longitudinal locking portion (102) includes a plurality of cantilevered fingers (110) provided with longitudinally extending teeth (112) on internal surfaces thereof. A nut (108) can be tightened in order to bias the cantilevered arms (110) towards a pusher (128) such that the teeth (112) indent the outer surface of the pusher (128) to produce a strong and stable locking connection thereto. The radial locking section (104) latches onto the assembly integral with the sheath (164) so as to provide a radial locking action as well as a longitudinal locking action. The locking unit (100) provides a strong and reliable locking action between the pusher (128) and the sheath assembly (164) and can be easily removed by a clinician or surgeon during the deployment process.

13 Claims, 5 Drawing Sheets

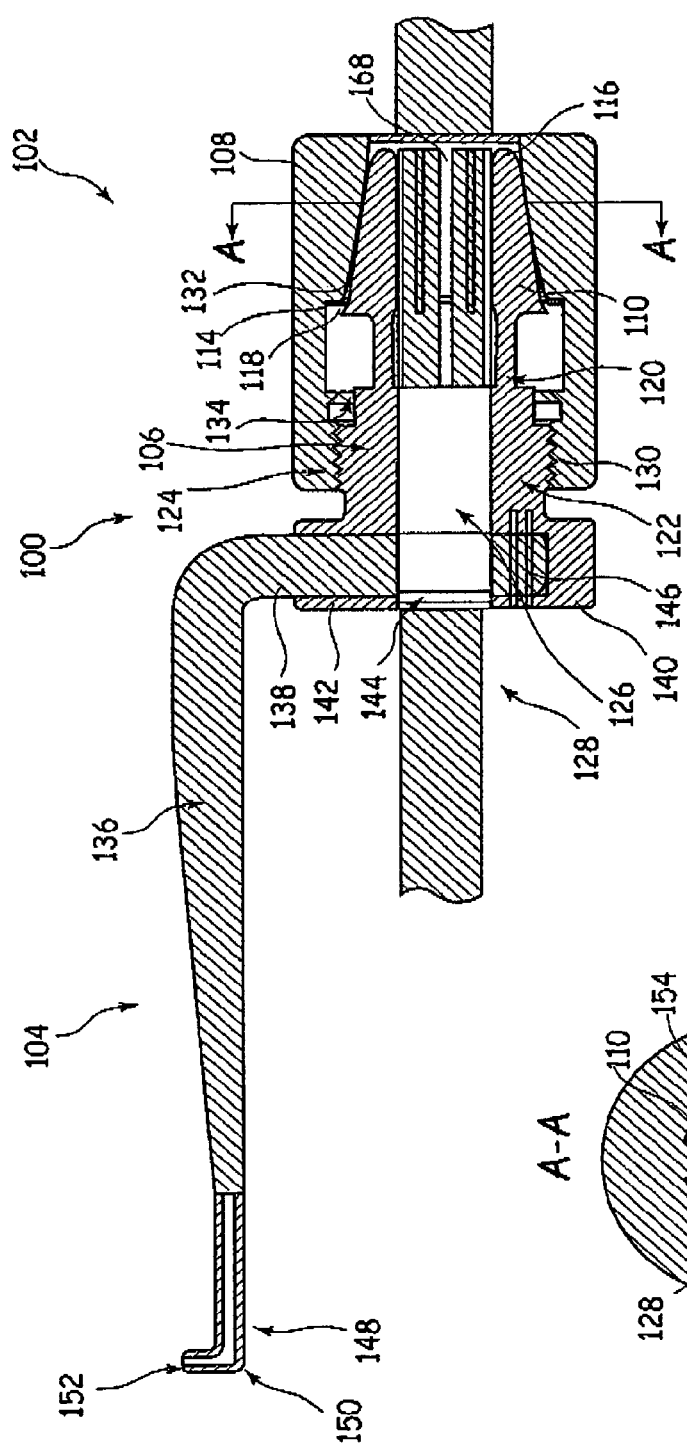
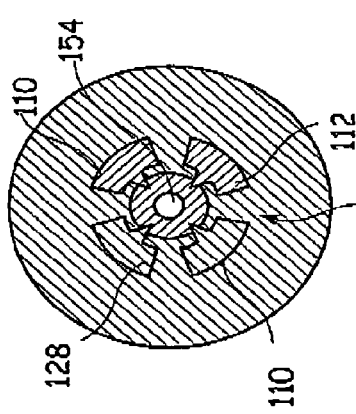
FIG. 3
FIG. 4

LOCKING DEVICE FOR SHEATH OR CATHETER

CROSS-REFERENCE TO RELATED APPLICATIONS

This application claims priority of provisional application Ser. No. 60/922,789, filed Apr. 11, 2007.

TECHNICAL FIELD

The present invention relates to a locking unit for locking two or more elements of an intraluminal device, such as a catheter, an introducer device or the like.

BACKGROUND OF THE INVENTION

Introducer devices for introducing intravenously a stent, stent graft or other implant or prosthesis are typically provided with an outer sheath within which there is provided a deployment mechanism such as a pusher rod and dilator. The sheath has the function of containing the various components of the introducer device and in particular the implant therewithin during the intraluminal introduction procedure. This flexes and twists as it passes through the various lumens of the patient, until it reaches the location at which the device being carried needs to be implanted. The sheath is typically of a construction that it is flexible so can be passed relatively easily through lumens of a patient and yet is able to withstand rotational torque, which is important during the implant placement process, for example for rotating the implant at the implantation site to ensure that it is implanted in the correct orientation. For this purpose, the sheath is of a length that extends, normally, to a dilator tip at the distal end of the introducer device and also to outside the insertion site in the patient, for example to outside the femoral artery. This end is typically termed the proximal end. This proximal end of the sheath typically has fitted integral therewith a plurality of manipulation elements for controlling the introduction of the sheath into the patient, the release of the implant, as well as for supplying various fluids during the medical procedure, such as saline solution or necessary medicaments.

Typically, the implant is located at the end of a pusher rod, which is itself flexible, which extends from the proximal to the distal ends of the deployment device and within the sheath.

It is necessary for the implantation procedure to be able to lock the pusher rod and the sheath together and a number of devices have been disclosed in the past.

For example, U.S. Pat. No. 5,064,414 discloses a locking clip which is clipped both to the pusher and to one of the grasping tabs of the sheath, the grasping tabs forming a handle for use by the surgeon. This locking unit limits the longitudinal movement of the pusher rod relative to the sheath until it is unlocked. However, the locking unit allows for rotation of the pusher relative to the sheath and some axial movement of the proximal end of the pusher relative to the proximal end of the sheath.

SUMMARY OF THE INVENTION

The present invention seeks to provide an improved locking unit for locking a sheath to a tubular or rod-like member to be held therewithin.

According an aspect of the present invention, there is provided a locking unit for a medical deployment device, which medical device is provided with a sheath element located over an inner tubular or rod-like insert member; the sheath element and inner member being movable relative to one another; the locking unit including at least one resiliently deformable engagement member provided with one or more teeth able to grip onto an outer surface of the insert member.

Advantageously, there are provided a plurality of deformable engagement members.

The teeth have the advantage of providing a strong connection of the locking unit to the insert member without requiring tight contact of a large surface area of components of the locking unit. This has the advantage of facilitating the release of the locking unit from the insert member.

In the preferred embodiment, there are provided a plurality of engagement members arranged in an annular form and a biasing member is provided with at least one biasing surface operable to bias the flexible members towards a reduced annular form and thereby into a locking position.

There is preferably provided a locking nut operable to bias the engagement member or members towards a locking position.

The nut is advantageously provided with an internal tapering surface operable to bias the engagement member or members in the locking direction. Advantageously, the biasing surface is a frusto-conical surface.

It is preferred that the or each engagement member is provided with an outer surface for contact with the internal tapering surface of the nut which is curved in a longitudinal direction thereof.

A locking unit in this form is able to prevent movement of the sheath towards the proximal end of the insert member.

The device preferably includes a radial locking member. Advantageously, the radial locking member includes an engaging element operable to engage a feature of the assembly. Most preferably, the feature is a protrusion from an element of the sheath assembly, in the preferred embodiment a port of a fluid chamber provided in the sheath assembly.

The radial locking member advantageously includes a forked latching element. Advantageously, the latching member is releasable from a locked condition by a twisting action. Thus, the latching element is preferably of a type which can be slid off a holding post integral with a sheath or sheath assembly. This enables easy removal of the locking unit from the sheath assembly by the surgeon, which is required in some instances during the intravenous medical procedures.

According another aspect of the present invention, there is provided a locking unit for a medical deployment device provided with a sheath element located over an inner tubular or rod-like member, the locking unit including a forked latching element for latching the sheath to the insert member.

It has been found that when the locking unit is locked to the introducer assembly prior to sterilisation, the act of sterilisation of the assembly softens the material of the insert member and as a result facilitates the unlocking of the locking unit during a medical procedure.

Advantageously, this latch member is arranged to prevent longitudinal and rotational movement of the sheath relative to the insert member.

It is preferred that both longitudinal and rotational movements are blocked. This has the advantage of reducing the relative torque between the sheath and the insert element, with the result that any movement of the insert element, such as the pusher, or of the sheath by whatever means ensures that such rotational movement causes rotation of the distal end of the introducer assembly as a cohesive unit. This is particularly advantageous for ensuring correct rotation and therefore placement of an implant in a patient. Of course, in cases where the introducer assembly is of a type which provides a medical treatment, rather than supplying an implant into a patient, this also ensures that any tool, medicament or the like, is located accurately at the desired position and orientation, without undue movement of the various components of the assembly relative to one another.

The preferred embodiment thus provides a locking unit for locking a pusher to a sheath assembly. The locking unit includes a longitudinal locking portion and a radial locking portion. The longitudinal locking portion includes a plurality of cantilevered fingers provided with longitudinally extending teeth on internal surfaces thereof. A nut can be tightened in order to bias the cantilevered arms towards a pusher such that the teeth indent the outer surface of the pusher to produce a strong and stable locking connection thereto. The radial locking section latches onto the assembly integral with the sheath so as to provide a radial locking action as well as a longitudinal locking action. The locking unit provides a strong and reliable locking action between the pusher and the sheath assembly and can be easily removed by a clinician or surgeon during the deployment process.

BRIEF DESCRIPTION OF THE DRAWING

Embodiments of the present invention are described below, by way of example only, with reference to the accompanying drawings, in which:

FIG. 3 is a cross-sectional view in side elevation of an embodiment of locking unit;

FIG. 4 is a view of the device of FIG. 3 in cross-section taken along line A-A of FIG. 3;

DETAILED DESCRIPTION

It is to be understood that the Figures are schematic and do not show the various components in their actual scale. In many instances, the Figures show scaled up components to assist the reader.

In this description, when referring to a deployment assembly, the term distal is used to refer to an end of a component which in use is furthest from the surgeon during the medical procedure, including within a patient. The term proximal is used to refer to an end of a component closest to the surgeon and in practice in or adjacent an external manipulation part of the deployment or treatment apparatus.

On the other hand, when referring to an implant such as a stent or stent graft, the term proximal refers to a location which in use is closest to the patient's heart, in the case of a vascular implant, and the term distal refers to a location furthest from the patient's heart.

Figure 1:
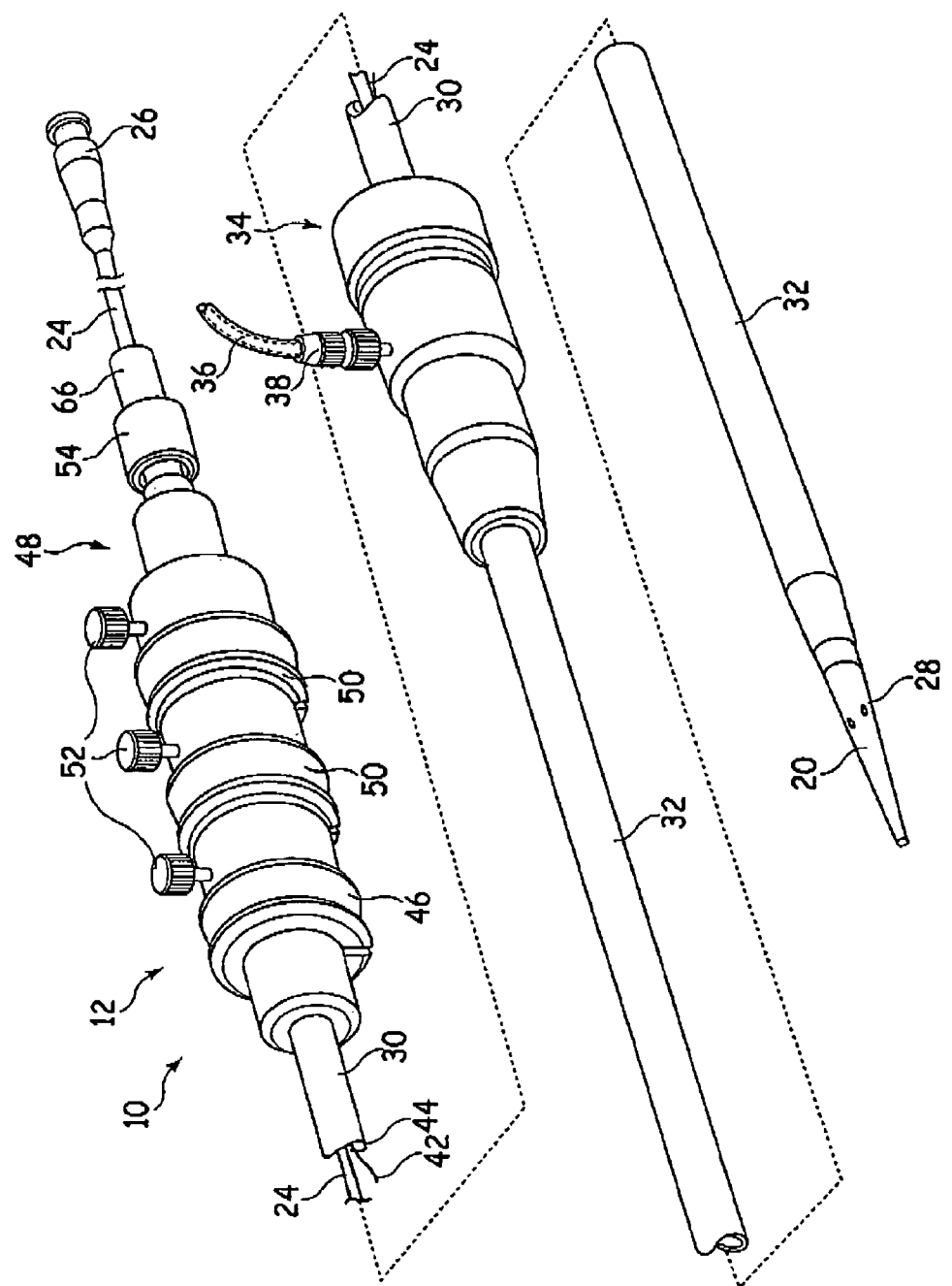
FIGS. 1 and 2 show an example of a deployment device.
Figure 2:
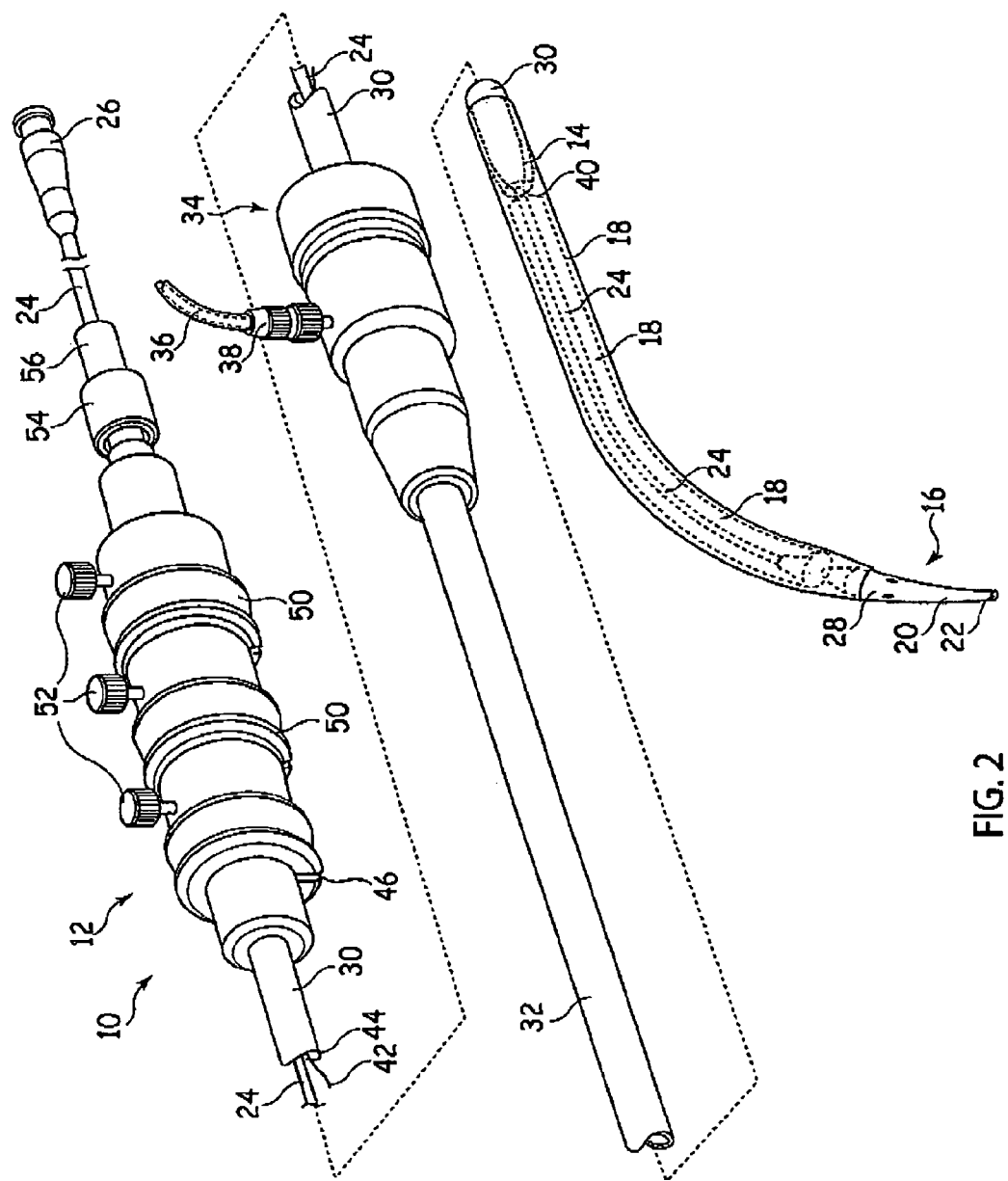

Referring to FIGS. 1 and 2, an implant deployment device 10 includes an external manipulation section 12, a proximal attachment region 14 and a distal attachment region 16. The proximal attachment region 14 and the distal attachment region 16 secure the two ends of the implant 18. During the medical procedure to deploy the implant 18, the proximal and distal attachment regions 14 and 16 will travel through the patient's vasculature, in this example, to a desired deployment site. The external manipulation section 12 at the proximal end of the implant deployment device 10, which is operated by a surgeon to manipulate the introducer, remains outside of the patient throughout the procedure.

The distal attachment region 16 of the implant deployment device 10 includes a dilator tip 20, which is typically provided with a bore 22 therein for receiving a guide wire (not shown) of conventional type. The longitudinal bore 22 also provides a channel for the introduction of medical reagents. For example, it may be desirable to supply a contrast agent to allow angiography to be performed during placement and deployment phases of the medical procedure.

An inner catheter or cannula 24, conventionally made from a flexible thin walled metal tube, is fastened to the dilator tip 20. The inner catheter 24 is flexible so that the implant deployment device 10 can be advanced along a relatively tortuous vessel, such as a femoral artery, and so that the distal end of the implant deployment device 10 can be longitudinally and rotationally manipulated. The inner catheter 24 carries a stent 18 or other device to be implanted in the patient. The catheter 24 extends through the implant deployment device 10 to the manipulation section 12, terminating at a connection device 26, in conventional manner.

The connection device 26 is designed to accept a syringe to facilitate the introduction of reagents into the inner catheter 24 and for this purpose is typically provided with a threaded luer lock connection.

Where provided, a pusher sheath or rod 30 (hereinafter referred to as a pusher member), typically made from a plastics material, is mounted coaxial with and radially outside of the inner catheter 24. The pusher member 30 is "thick walled", that is the thickness of its wall is preferably several times greater than that of the guide wire catheter 24. In some instances, the pusher member 30 and the inner catheter 24 are the same component, possibly having different outer diameters at the location at which the stent 18 is to be carried.

A sheath 32 extends coaxially over and radially outside of the pusher member 30. The pusher member 30 and the sheath 32 extend distally to the manipulation region 12.

The implant 18, which may be a stent, a stent-graft or any other implant or prosthesis deliverable by the implant deployment device 10, is retained in a compressed condition by the sheath 32. The sheath 32 extends proximally to a sheath manipulator and haemostatic sealing unit 34 of the external manipulation section 12. The haemostatic sealing unit 34 includes a haemostatic seal (not shown) and a side tube 36 held to the unit 34 by a conventional luer lock 38.

The sheath manipulator and haemostatic sealing unit 34 also includes a clamping collar (not shown) that clamps the sheath 32 to the haemostatic seal and a silicone seal ring (not shown) that forms a haemostatic seal around the pusher member 30. The side tube 38 facilitates the introduction of medical fluids between the pusher member 30 and the sheath 32. Saline solution is typically used.

During assembly of the implant deployment device 10, the sheath 32 is advanced over the proximal end of the dilator tip 20 of the proximal attachment region 16 while the implant 18 is held in a compressed state by an external force. A suitable distal attachment (retention) section (not visible in this view) is coupled to the pusher member 30 and retains a distal end 40 of the prosthesis 18 during the procedure. The distal end of the prosthesis 18 may be provided with a loop of material (not shown) through which a distal restraining wire 42 extends. The distal restraining wire also extends through an aperture (not shown in FIGS. 1 and 2) in the proximal attachment section 40 into an annular region 44 between the inner catheter 24 and the pusher member 30. The distal restraining wire 42 extends through the annular space 44 to the manipulation region 12 and exits the annular space 44 at a distal wire release mechanism 46.

A proximal portion of the external manipulation section 12 includes at least one restraining wire actuation section 50 mounted on a body 48, in turn mounted onto the pusher member 30. The inner catheter 24 passes through the body 48. The distal wire release mechanism 46 and the proximal wire release mechanism 50 are mounted for slidable movement on the body 48.

The positioning of the proximal and distal wire release mechanisms 46 and 50 is such that the proximal wire release mechanism or mechanisms 50 must be moved before the distal wire release mechanism 46 can be moved, such that the proximal end of the implant, that is the end of the implant which will be upstream in the direction of fluid flow in the patient's vasculature, is released first. Therefore, the distal end of the implant 18 cannot be released until a self-expanding zigzag stent thereof has been released. Clamping screws 52 prevent inadvertent early release of the prosthesis 18. A haemostatic seal (not shown) is included so that the release wires can extend out through the body 48 without unnecessary blood loss during the medical procedure.

A proximal portion of the external manipulation section 12 includes a pin vise 54 mounted onto the proximal end of the body 48. The pin vise 54 has a screw cap 56. When screwed in, vise jaws (not shown) of the pin vise 54 clamp against or engage the inner catheter 24. When the vice jaws are engaged, the inner catheter 24 can only move with the body 48 and hence it can only move with the pusher member 30. With the screw cap 56 tightened, the entire assembly can be moved together as one piece.

Once the implant deployment device 10 is in the desired deployment position, the sheath 32 is withdrawn to just distal of the proximal attachment section 14. This action releases the middle portion of the implant 18, in this example a stent or stent-graft, so that it can expand radially. Consequently, the stent or stent-graft 18 can still be rotated or lengthened or shortened for accurate positioning. The proximal end of the self-expanding stent however, is still retained at the distal attachment region 16 by means of the restraining wires. Also, the distal end of the stent or stent-graft 18 is still retained within the sheath 32.

Next, the pin vise 54 is released to allow small movements of the inner catheter 24 with respect to the pusher member 30 to allow the stent or stent-graft 18 to be lengthened, shortened, rotated or compressed for accurate placement in the desired location within the lumen. X-ray opaque markers (not shown) may be placed along the stent or stent-graft 18 to assist with placement of the implant.

When the proximal end of the stent or stent-graft 18 is in place, the proximal restraining wire (not shown) is withdrawn by movement of the proximal wire release mechanism 50. The proximal wire release mechanism 50 and the proximal restraining wire can be completely removed by passing the proximal wire release mechanism 50 over the pin vise 54, the screw cap 56 and the connection unit 26.

Next, the screw cap 56 of the pin vise 54 is loosened, after which the inner catheter 24 can be pushed in a distal direction, that is towards the inside of the patient, so as to move the dilator tip 20 in a distal direction. This fully releases the proximal end of the stent or stent-graft 18, allowing it to expand so as to engage the lumen walls of the artery or vein. From this stage on, the proximal end of the stent or stent-graft 18 cannot be moved again.

Once the proximal end of the stent or stent-graft 18 is anchored, the sheath 32 is withdrawn proximally of the proximal attachment section 14, which withdrawal allows the distal end of the stent or stent-graft 18 to expand. Until this point and in particular until the distal release mechanism 46 is actuated to release the distal restraining wires from the distal end of the stent 18, the distal may still be repositioned as needed.

For some procedures, the sheath 32 may be left in place after expansion of the implant 18. The pusher member 30 and inner catheter 24 may be withdrawn and replaced by a further component, using the sheath 32 as a guide.

A problem can occur when using prior art introducer devices and in particular when it is necessary to twist the introducer device in order to rotate the distal end of the introducer device to ensure correct orientation of that end of the device and, in the case of deployment of a prosthesis or implant, correct orientation of the implant in the patient. With prior art devices, it can occur that when the surgeon attempts to rotate the proximal end of the deployment device, that is the end external to the patient, there is relative rotation between the pusher rod and the sheath and therefore incorrect rotation of the distal end of the deployment device. This can result in incorrect placement of an implant and in some cases can also lead to twisting of the implant because of the torque generated at the between the sheath and the pusher member at the distal end of the device.

Referring now to FIG. 3, there is shown a cross-sectional view in side elevation of the preferred embodiment of locking unit 100. This embodiment includes two portions, a first portion 102 which provides a longitudinal locking function and a second portion or arm 104 which provides a radial locking action.

The first portion 102 is formed of an inner gripping member 106 and an outer nut 108. The inner gripping member 106 is provided with a plurality of cantilevered fingers 110, in this embodiment there being four such fingers 110 although other numbers of fingers may be provided. Along an inner surface of each finger 110 and extending along its longitudinal axis, there is provided a tooth 112, which preferably has a triangular shape in longitudinal cross-section, as shown in particular in FIG. 4.

The outer surface 114 of each cantilevered finger 110 is curved in a convex manner in its longitudinal direction, as well as being curved in its radial direction. These outer surfaces 114 also widen from the ends 160 of each cantilevered finger, as is readily visible in FIG. 3. At the end of the curved section of each surface 114, there is provided an outwardly extending flange or shoulder 118 and beyond that a section 120 of reduced outer diameter. As will be apparent from FIG. 3 in particular, the flange 118 is discontinuous, being located on the cantilevered portions of the fingers 110 and thus split by the gaps 168 between the fingers.

The reduced outer diameter section 120 terminates, in this embodiment, at the ends of the cantilevered fingers 110 and is integral with an annular portion 122. The annular portion 122 is provided with an external screw thread 124.

The cantilevered fingers 110 and the annular portion 122 provide an internal bore 126 for the passage of a pusher 128 therethrough or for the passage of any other catheter or elongate insert of the type used for intraluminal delivery or treatment.

The inner gripping member 106 is preferably made of a plastics material, although it could be made of any other material which allows the cantilevered fingers 110 to be resiliently deformable, at least at the zone 120 of reduced outer diameter.

The nut 108 includes at one end an internal threaded section 130 with threads which are matched to the external threads 124 of the inner gripping member 106.

At the other end of the nut 108, there is provided an internal tapering surface 132 which in this embodiment provides a frusto-conical surface tapering away from the internal threaded section 130 and in the same direction as the taper of the outer surfaces 114 of the cantilevered fingers 110. In this embodiment, the surface forming the internal tapering section 132 is substantially straight, such that when the nut 108 is fitted onto the inner gripping member 106, as shown in FIG. 3, there is only partial contact between the inner surface of the tapering section 132 and the outer surfaces 114 of the cantilevered fingers 110. This has the advantage of providing the desired biasing action on the cantilevered fingers 110, as described below, while reducing the surface area contact between the cantilevered fingers 110 and the nut 108, thereby to reduce any friction between these two components. Moreover, this tangential contact of the outer surfaces 114 of the cantilevered fingers 110 and the internal tapering surface 132 maintains a good closing action on the fingers 110 as the nut 108 is tightened.

Between the internal threaded section 130 and the tapering section 132 of the nut 108, there is provided an internally extending annular flange 134 which provides a second shoulder facing and opposite to the outwardly extending annular flange or shoulder 118 of the inner gripping member 106.

The nut 108 is preferably also made of a plastics material and most preferably a material which is substantially rigid. Advantageously, the outer surfaces of the nut 108 are provided with one or more markings to assist a user in rotating the nut 108 in locking and/or unlocking directions, as described below.

The radial locking section 104 is provided with a leg member 136 which is bent substantially at 90°, in this embodiment, to provide a fastening portion 138 thereof. This fastening portion 138 extends into a blind bore 142 of an enlarged annular element 140 formed integrally with the inner gripping member 106. The fastening portion 138 is provided with a circular opening 144 which aligns with the internal bore 126 of the internal gripping member 106 and is fixed to the enlarged annular element 140, in this embodiment, by means of one or more pins 146, as shown in FIG. 3.

The leg member 136 extends from the 90° bend in a direction substantially parallel to the longitudinal axis of the inner gripping member 126 and ends in a forked foot section 148. The section 148 includes first and second feet 140 (only one being visible in FIG. 3), each of which is provided with a perpendicularly extending latching element 152.

The leg member 136 tapers towards the forked foot section 148, which has the effect of increasing the flexibility of the radial locking section 104 at the foot section 148. This facilitates the fitting and removal of the locking unit 100 from an introducer device, as described in further detail below.

The leg member 136 is preferably made of the same material as the inner gripping member 106, that is of any suitable plastics material.

Referring now to FIG. 4, there is shown a cross-sectional view of the device taken along line A-A of FIG. 3. There can be seen located within the cantilevered fingers 110 a pusher 128, of conventional form, and within that a wire guide 154, also of conventional form.

The teeth 112 of the cantilevered fingers 110 dig into the outer surface of the pusher 128, preferably not to the extent of damaging that outer surface but simply producing a recoverable indentation for gripping purposes. This has the advantage that a strong gripping effect can be achieved without requiring a large surface area contact to be provided between the cantilevered fingers 110 and the outer surface of the pusher 128 or other longitudinal element positioned in the bore 126 inside the inner gripping member 106.

Figure 5:
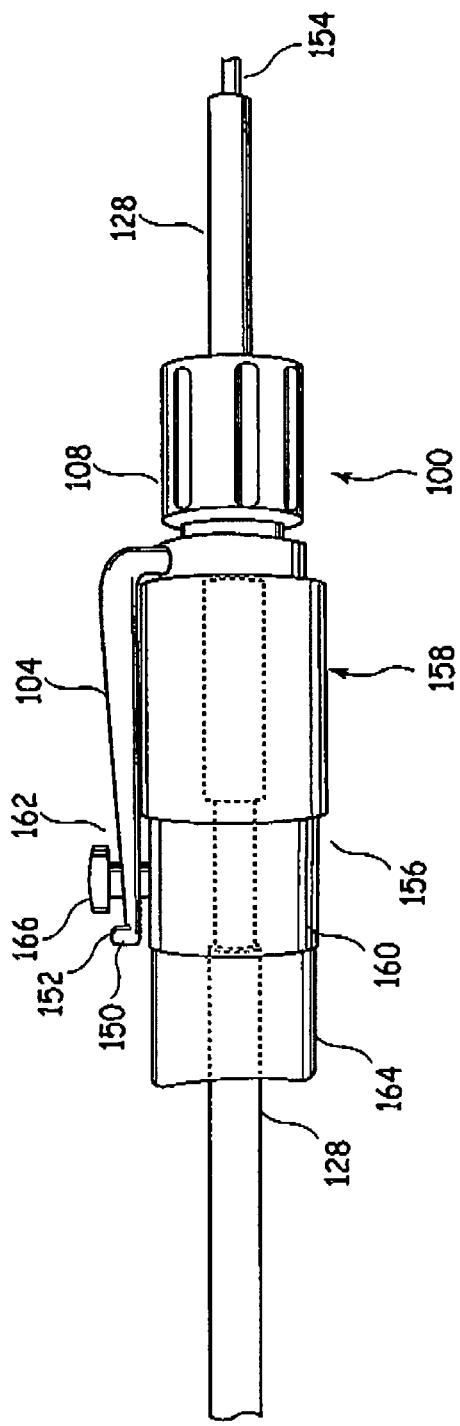
FIG. 5 is a side elevational view of the locking unit of FIG. 3 fitted to a sheath and pusher assembly.

FIG. 5 shows in schematic form a view of the device 100 as it might be provided in use.

The locking unit 100 is fitted to a deployment device of a type similar to that shown in FIGS. 1 and 2, in place of the pin vice 54 and screw cap 56.

The locking unit 100 fits over the pusher 128 and wire guide 154 and is aligned with and in practice abuts the external assembly 156. This assembly 156 typically includes a haemostatic valve held within a control member 158, adjustable in order to open and close the haemostatic valve as necessary, and chamber 160 for the introduction of fluids into the introducer device, such as medicaments or other treatment materials of a type known in the art. A sheath 164 extends from the chamber 160 in the distal direction of the delivery device, also being well known in the art.

The chamber 160 is fluidically coupled to the interior of the sheath 164 and is provided with a port 162 for the introduction of medicaments or other treatment fluids, such as saline solution. The port 162 is provided with an enlarged head 166, which is typically threaded so as to engage with a luer lock (not shown) of conventional form.

The forked foot section 104 extends over the haemostatic valve assembly 158 and the chamber 160 such that the feet 150 thereof extend either side of the port 162 with the latching elements 152 extending in a direction towards the enlarged head 166, as shown in FIG. 5.

When the locking nut 108 of the locking unit 100 is in an unlocked position, the internal tapered surface 132 thereof applies no or substantially no biasing force against the cantilevered fingers 110, allowing them to hold their unbiased open positions. This enables the pusher 128 to slide freely within the locking unit 100. It can also be rotated therewithin.

The nut 108 can be rotated to its closed position, that is rotated such that it moves towards the left as in the views of FIGS. 3 and 5 by virtue of the engagement of the threaded elements 124 and 130. This causes a progressively stronger biasing force to be applied to the cantilevered fingers 110 by virtue of the reducing diameter of that part of the tapering section 132 of the nut 108 which applies pressure to the fingers 110. This biasing action causes the fingers 110 to be urged towards the pusher 128 and eventually for the teeth 112 to dig into the pusher 128, as shown in FIG. 4. In practice, as the fingers 110 are pushed inwardly, the gaps 168 between the fingers 110 diminish.

Once the teeth 112 embed into the outer surface of the pusher 128, they provide a very strong and reliable locking action of the locking unit 100 to the sheath 128. The leg member 136 and, in particular, the forked foot section 148 lock onto the port 162 and prevent the valve/chamber/sheath assembly 158-164 from rotating relative to the locking unit 100 and thereby relative to the pusher 128. The latching elements 152 at the end of the feet 150 prevent the assembly 158-164 from being pulled away from the locking unit 100 and therefore prevent longitudinal withdrawal of the assembly 158-164 from the pusher 128 in a direction away from the locking unit 100.

Therefore, when locked, the locking unit 100 provides a strong and reliable locking action of the pusher 128 relative to the sheath 164 and a locking action which is much stronger and much more reliable than prior art devices. The skilled person will appreciate that a nut of a luer lock is fitted onto the enlarged head 166, the latching elements 152 provide very little play between the locking unit 100 and the assembly 158-164 in the longitudinal direction.

Typically, the delivery device 10 is provided with the locking unit 100 already fitted thereon and in a locked condition. This fixes the pusher 128 relative to the sheath 164 and therefore provides a strong unitary structure for the delivery of a stent, stent graft, occlusion device, filter or any other prosthesis or implant to be delivered intraluminally into a patient. Moreover, the various elements of the assembly are typically assembled and subsequently sterilised by a suitable sterilisation gas (for example ethylene oxide), before being placed in a sealed bag or other container until used. Typically, pusher members are made of PVC or similar material. It has been found that during the sterilisation process the pusher material is softened by the sterilisation gas. This has been found to soften the material at the deformation zones of the pusher 128 produced by the teeth 112. This softening can to facilitate the unlocking of the nut 108 during the implantation process. The effect is such that surgeon or other clinician can easily unlock the nut 108 while holding the locking unit 100 and assembly 158-164 with one hand. This releases the surgeon or clinician's other hand for other medical procedures, which is of course a substantial benefit.

Thus, during a delivery procedure the delivery device, with the lock 110 fitted thereto and locked, is manipulated intravenously, typically from a femoral artery, to locate stent, stent graft or other implant or prosthesis to the desired site. The surgeon or clinician can manipulate the external or proximal section of the delivery device, both in a longitudinal direction and also rotationally, in order to rotate the distal end of the assembly and thus the device to be delivered while at it is at the desired delivery location inside a lumen of the patient. Once the surgeon or clinician is satisfied that the device to be delivered is in the correct location and orientation, the nut 108 is released by unscrewing it. The nut 108 does not come off the inner gripping member 106, by virtue of the above-described internal shoulder 134 of the nut 106 abutting the shoulder 108 of the inner gripping member 106. Thus, the threaded section 130 of the nut 108 can be completely unscrewed from the threaded section 124 of the internal gripping member 106 but without risk of the nut 108 coming loose from the assembly. This has the advantage that the surgeon or clinician does not need to worry about components of the delivery assembly coming loose during the deployment procedure.

In many instances, it is desired to leave the sheath 164 (32 as shown in FIGS. 1 and 2) in place once the implant or prosthesis has been deployed, for example to carry out further medical procedures intravenously. In these cases, the pusher 128 is removed from the sheath assembly by withdrawing it completely and then leaving the sheath 164 in place within the patient. Once the pusher 128 has been removed, further catheters or other treatment devices are slid through the sheath 164, as is well known in the art. In such an event, it is desirable to remove the locking unit 100 because this is no longer needed.

Figure 6:
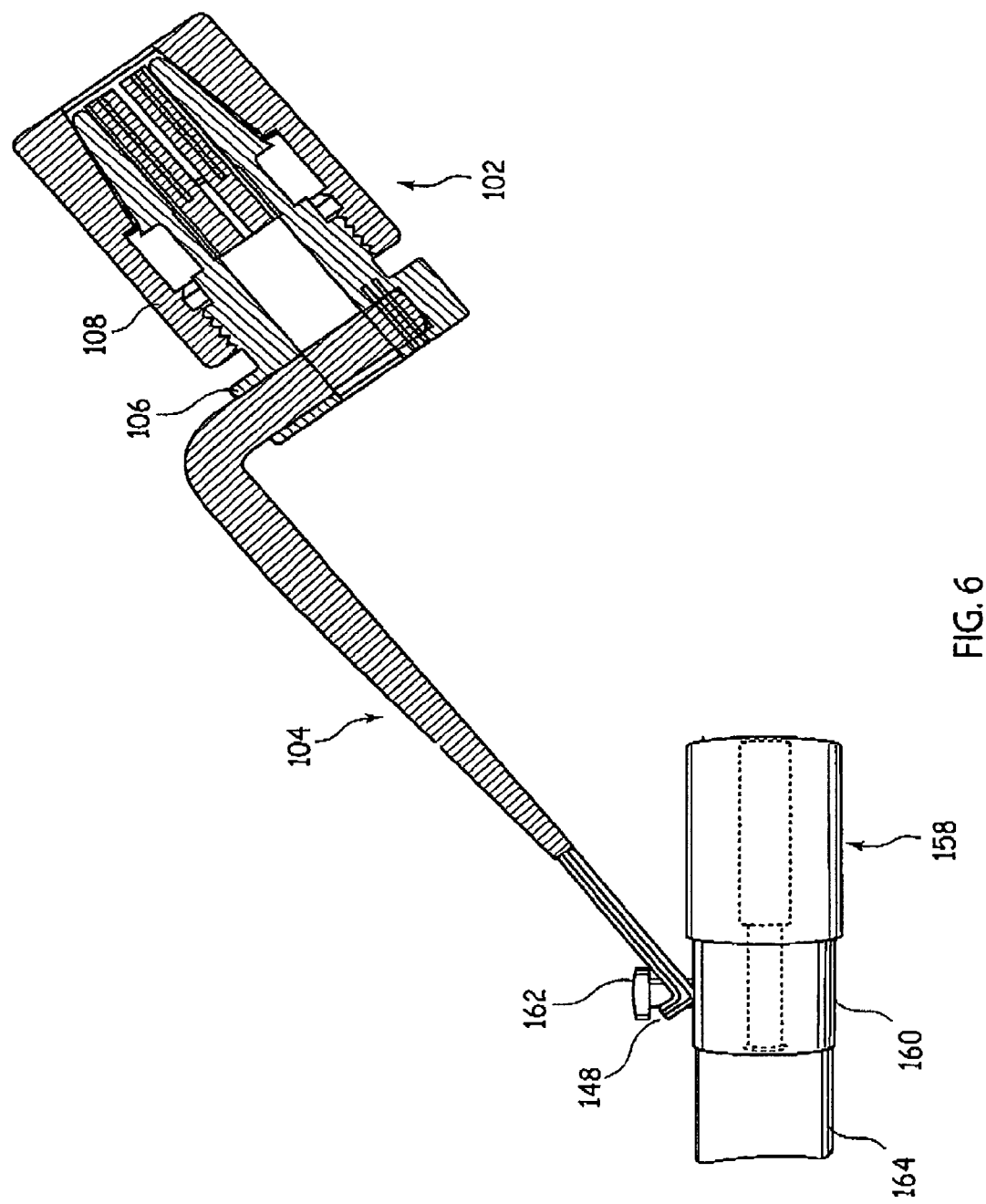
FIG. 6 is a schematic view of the locking unit of FIG. 3 being released from a sheath.

This can be easily achieved with the design of forked foot section 148 of the radial locking section 104 of the preferred embodiment. As can be see in FIG. 6, once the pusher 128 has been withdrawn from the delivery device and from within the locking unit 100 also, the locking unit 100 can be removed by pivoting the foot section 148 about the upstanding port 162 and thereby pivoting the perpendicularly extending latching elements 152 around the base of that port 162. This can be done easily by the surgeon or clinician, before being discarded.

Of course, it is also envisaged that in place of a forked foot section 148, the leg member 136 could be provided with a completely enclosed hole into which the port 162 can be fitted, in which case the locking unit 100 would typically be removed by unscrewing the syringe or tubing fitted to the port 162.

Referring again to FIG. 3, it will be appreciated in particular from this Figure that the generally annular flange or shoulder 118 provided on the inner gripping member 106 is located along an intermediate portion of the flexible cantilevered fingers 110. This has the advantage that, when the nut 108 is completely unscrewed from the threaded element 124 of the inner gripping member 106, application of a reasonably substantial force on the nut 108 away from the inner gripping member 106 will cause the cantilevered fingers 110 to bend inwardly and towards one another, having the effect of pushing the annular shoulders 118 inwardly also, with the result that the nut 108 can be removed from the inner gripping member 106. In some instances, a medical procedure might necessitate use of the locking unit 100 without the nut 108, for example when inserting a particularly large elongate element therein. This feature also facilitates the assembly of the nut 108 onto the inner gripping member 106. The design is such that the nut 108 cannot be pulled off the inner gripping member 106 when a pusher 128 or other element is located in the device 100, because the fingers 110 are not able to bend inwardly enough due to the presence of the pusher 128 to allow the flange 118 to clear the outer flange 134.

It will be appreciated that the locking unit 100 can lock to various external diameter elongate inserts, depending primarily upon the choice of gap 168 between the cantilevered fingers 110 and the dimensions of the frusto-conical surface 132 of the nut 108. It is envisaged that a variety of nuts 108 could be provided, with internal tapering sections 132 of differing dimensions, such that a different nut can be fitted to the same inner gripping member 106 to provide for locking of different ranges of diameters of pushers or other inserts.

The locking unit 100 provides a very strong and reliable locking connection between a pusher 128 or other device and the outer sheath which can be unlocked easily and in many instances with a single hand. This has significant advantages during the deployment procedure.

It will also be appreciated that although the preferred embodiment disclosed above is directed to a deployment device for delivery and deployment of an implant such as a stent or stent graft into an artery or vein of a patient, the device could equally be used for effecting treatments or for implanting devices in other locations on a patient, including in an organ.

The skilled person will understand that the invention features taught herein are not limited to the specific embodiments described and that they encompass alternatives and modifications within the knowledge and ability of the skilled person; and that it is the claims which specify the scope of this disclosure.

What is claimed is:

1. A locking unit comprising:
   at least one resiliently deformable engagement member provided with at least one tooth on an inner surface of the at least one resiliently deformable engagement member;
   a locking nut having a threaded section and at least one biasing surface, both the threaded section and the at least one biasing surface being operable to bias the at least one resiliently deformable engagement member towards a locking position; and
   including a radial locking member, wherein the radial locking member includes a forked latching element;
   the at least one tooth extending internally in a radial direction of the locking unit and being able to grip a medical device when the at least one resiliently deformable engagement member is positioned in the locking position.

2. A locking unit according to claim 1, wherein there is a plurality of resiliently deformable engagement members.

3. A locking unit according to claim 1, wherein there is a plurality of resiliently deformable engagement members arranged in an annular arrangement.

4. A locking unit according to claim 1, wherein said at least one biasing surface is formed by an internal tapering surface of said locking nut.

5. A locking unit according to claim 1, wherein the at least one biasing surface is frusto-conical.

6. A locking unit according to claim 1, wherein the at least one resiliently deformable engagement member is provided with an outer surface which is curved in a longitudinal direction thereof.

7. A locking unit according to claim 1, wherein the radial locking member includes an engaging element operable to engage the medical device.

8. A locking unit according to claim 7, wherein the engaging element is operable to engage a protrusion from an element of the medical device.

9. A locking unit according to claim 1, wherein the latching element is releasable from a locked condition by a twisting action.

10. A locking unit according to claim 1 further comprising: the forked latching element with a first foot and a second foot extending in a longitudinal direction over a medical device, the forked latching element for latching to the medical device and for blocking rotational movement of the medical device.

11. An intraluminal delivery device comprising:
a sheath element and an inner insert member, the sheath element being locatable over the inner insert member;
a locking unit including at least one resiliently deformable engagement member provided with at least one tooth on an inner surface of the at least one resiliently deformable engagement member;
a locking nut and at least one biasing surface, both the locking nut and the at least one biasing surface being operable to bias the at least one resiliently deformable engagement member towards a locking position; and
the at least one tooth extending internally in a radial direction of the locking unit and being able to grip the inner insert member when the at least one resiliently deformable engagement member is positioned in the locking position.

12. An intraluminal delivery device according to claim 11, provided with an implant or prosthesis for implantation.

13. A locking unit comprising:
at least one resiliently deformable engagement member provided with at least one tooth on an inner surface of the at least one resiliently deformable engagement member;
a locking nut having a threaded section and at least one biasing surface, both the threaded section and the at least one biasing surface being operable to bias the at least one resiliently deformable engagement member towards a locking position; and
the at least one tooth extending internally in a radial direction of the locking unit and being able to grip a medical device when the at least one resiliently deformable engagement member is positioned in the locking position; and
a forked latching element with a first foot and a second foot extending in a longitudinal direction over the medical device, the forked latching element for latching to the medical device and for blocking rotational movement of the medical device.

* * * * *